United States Patent [19]

Mitsuhashi

[11] 4,371,265
[45] Feb. 1, 1983

[54] DOT PERCENTAGE MEASURING DEVICE

[75] Inventor: Yuji Mitsuhashi, Fujisawa, Japan

[73] Assignee: Dai Nippon Insatsu Kabushiki Kaisha, Tokyo, Japan

[21] Appl. No.: 190,171

[22] Filed: Sep. 23, 1980

Related U.S. Application Data

[62] Division of Ser. No. 941,174, Sep. 11, 1978, Pat. No. 4,264,210.

[30] Foreign Application Priority Data

Sep. 13, 1977 [JP] Japan .............................. 52-110150
Mar. 25, 1978 [JP] Japan .............................. 53-38440

[51] Int. Cl.$^3$ ............................................ G01N 21/01
[52] U.S. Cl. .................................................. 356/432
[58] Field of Search ....................... 356/430, 432–434, 356/443–445; 355/68; 250/228, 239

[56] References Cited

U.S. PATENT DOCUMENTS

| | | | |
|---|---|---|---|
| 3,053,181 | 9/1962 | Jorgensen | 356/445 X |
| 3,375,751 | 4/1968 | Engborg et al. | 356/443 |
| 3,393,602 | 7/1968 | Stouffer | 356/445 |
| 4,029,958 | 6/1977 | Wright | 356/428 X |

Primary Examiner—Bruce Y. Arnold
Attorney, Agent, or Firm—Koda and Androlia

[57] ABSTRACT

In printing with dots, a dot percentage is one of the important factors which determine the quality of a printed matter, and accordingly it is essential to control the dot percentage throughout the printing process from makeup to printing. In order to readily and quickly measure the dot percentage with high accuracy, a microscope section and a display section are formed as one unit, and a correction circuit for light transmittance is provided.

1 Claim, 45 Drawing Figures

(PRIOR ART)
F I G. 1(A)
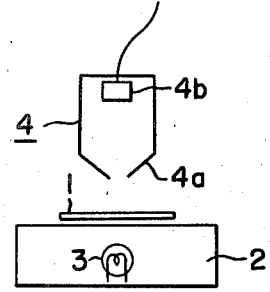
(PRIOR ART)
F I G. 1(B)
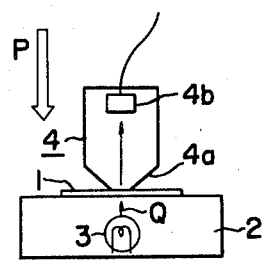
F I G. 2
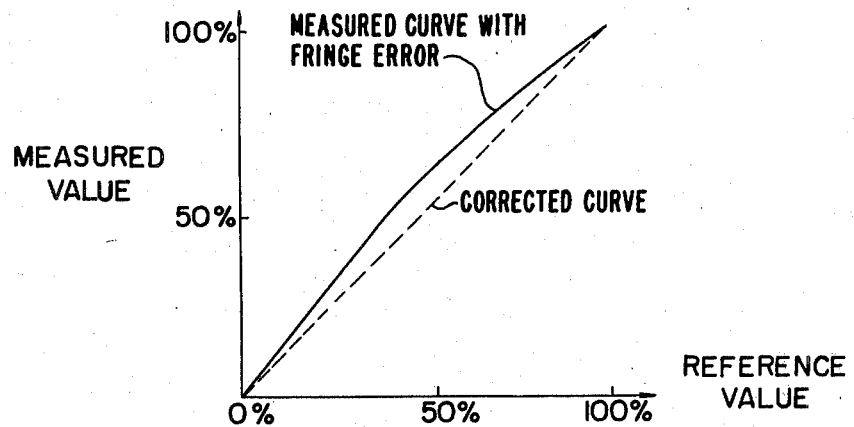
F I G. 3

F I G. 17
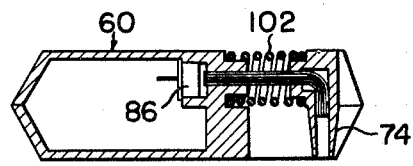
F I G. 18
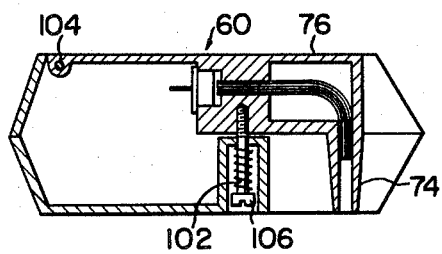
F I G. 19
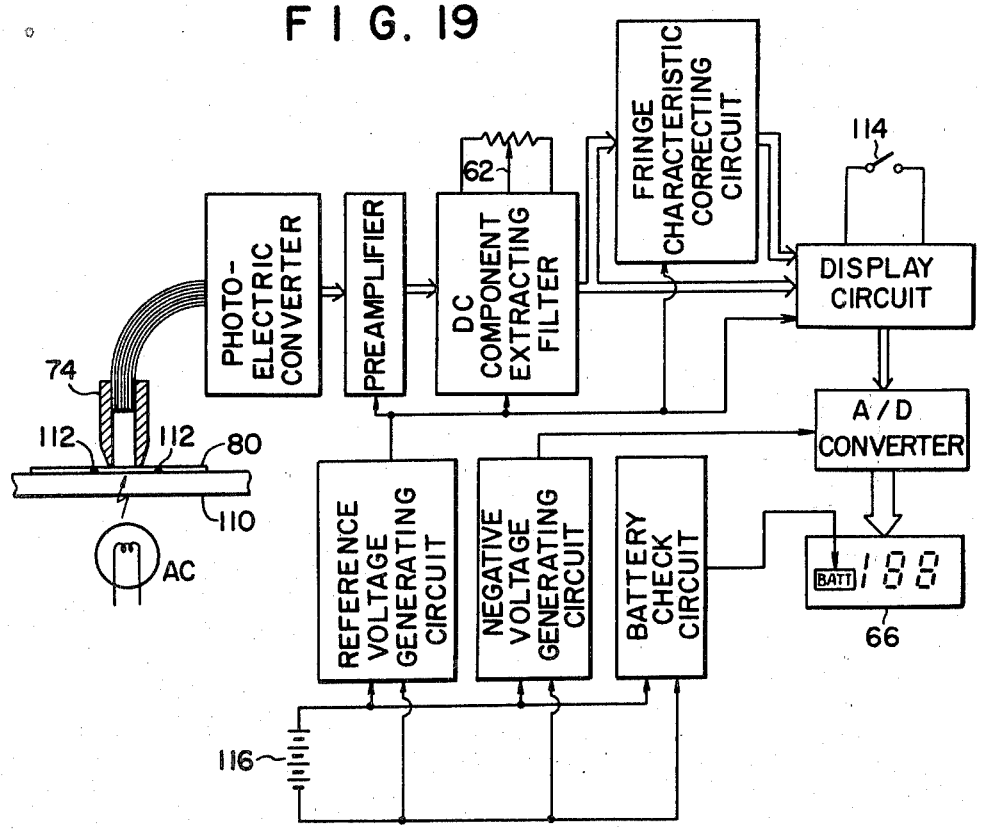

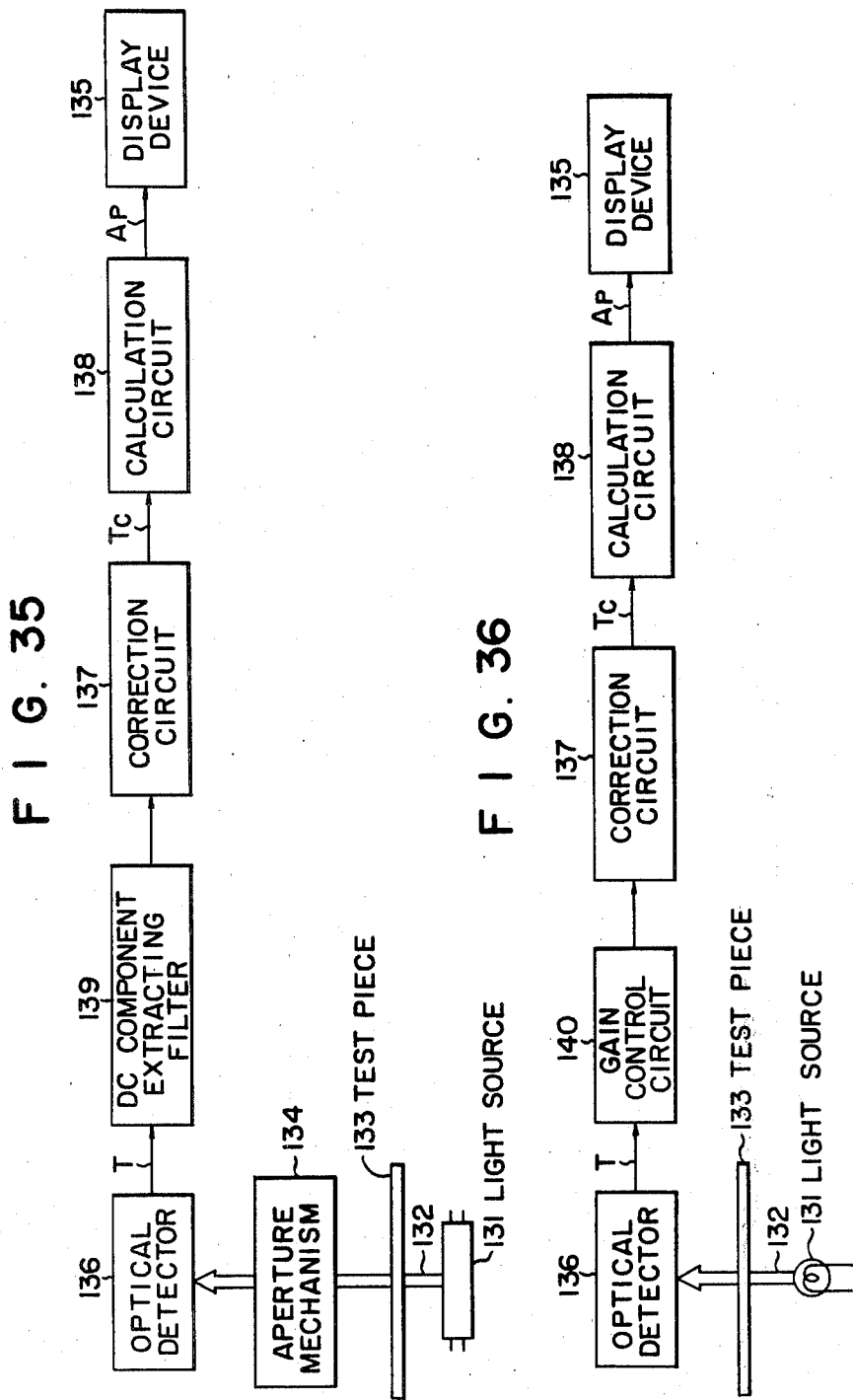

(A)           (B)

(A)           (B)

DOT PERCENTAGE MEASURING DEVICE

This is a division of application Ser. No. 941,174, filed Sept. 11, 1978 now U.S. Pat. No. 4,264,210.

BACKGROUND OF THE INVENTION

This invention relates to dot percentage measuring devices.

The shading of a continuous tone copy such as a photograph is expressed by using dots of different sizes in printing. In this method, the continuous tone copy is photographed through a screen or a contact screen to obtain a film called a screen negative or a screen positive in which the shading of the copy is expressed by dots different in size, and a printing plate is formed from this film.

A term "dot percentage" as used herein is a percentage of the total area of dots with respect to a unitary area in such a screen positive or a screen negative or a dot-printed matter. Accordingly, the value of dot percentage will greatly affect the tone and gradation of a printed matter.

When an obtained dot percentage is different from a predetermined one, it may be corrected by subjecting the screen positive or the screen negative to "reduction" which is one of the methods of correcting a dot percentage. In the reduction, the photographed film is washed with a so-called "reducer" to reduce the density of the picture. In the case of a dot-printed matter, a portion around a dot, which is low in density and is called "a fringe", on the film becomes transparent by the reduction process; that is, the dot percentage is decreased to correct the values of the printed matter. Thus, in printing with dots, the dot percentage is one of the important factors which determined the quality of a printed matter, and accordingly it is essential to control the dot percentage throughout the printing process from makeup to printing.

In an off-set retouch process, it is necessary to measure dot percentages after reduction has been carried out, and to ensure the configurations of dots, especially whether the dots are deformed or not.

In the case where the dot area becomes considerably smaller by excessive reduction or where measurement result indicates smaller dots, it is necessary that the dots are photographed again and are compared with the previous ones. Heretofore, dots are, in general, evaluated by visual inspection. However, the visual inspection is disadvantageous in that it involves personal errors and therefore it is necessary to provide a skilled person for the visual inspection. Since halftone-photographed dots are soft dots including fringes, the inspector will read the size of dots including fringes through his sense of sight, and accordingly the size of dots thus read is larger than the real size of dots.

Furthermore, although the data actually required in a reduction process is not the absolute value of dot percentage, but rather the difference between the dot percentage before reduction and that after reduction, no device for indicating this latter amount has as yet been provided.

A conventional dot percentage measuring device of this type is shown in FIG. 1(A). A light emitting section 3 is provided inside a measuring table 2 on which an object 1 to be measured, such as a film, is placed, and a light receiving section 4 is movably provided above the measuring table 2 in such a manner that it can confront the light emitting section 3. The light receiving section 4 is made up of a cylindrical head 4a which is open at one end, and a light receiving element 4b such as a photo-electric conversion element. In measuring a dot percentage with this conventional measuring device, the object 1 to be measured is placed on the measuring table 2, and a portion to be measured of the object 1 is positioned at the measuring section of the device (or on the line connecting the light emitting section 3 and the light receiving section 4). Then, the light receiving section 4 is lowered in the direction of the heavy arrow P to confront the light emitting section 3 as shown in FIG. 1B, so that the upper opening edge of the head 4a is in close contact with the portion to be measured of the object 1. Under the conditions that the external light is shielded, the light emitting section 3 emits a predetermined intensity of light to irradiate the lower surface of the object 1 in the direction of the shorter arrow Q shown in FIG. 1(B) so that the light receiving element 4b in the light receiving section 4 receives light passed through the object 1, and the dot percentage of density of the object 1 is displayed by a display section (not shown) connected electrically to the light receiving element 4b.

However, the conventional measuring device is disadvantageous in the following points: The construction of the measuring device is intricate because the device is so designed that the light receiving section is movable towards the light emitting section as was described above. The operation of the measuring device is intricate and accordingly troublesome because positioning the measurement portion of the object 1 must be carried out before measurement and the upper opening edge of the head 4a must be brought into close contact with the measurement portion of the object 1. Therefore, in the case where a dot percentage of density measured should be corrected by reduction, it is necessary to carry out the following steps: After the object 1 is removed from the measuring table 2 and is subjected to reduction process by using a washing table or the like, the object 1 must be placed on the measuring table 2 again. This will increase labor and decrease work efficiency.

Measurement of a dot percentage is carried out in the processes of halftone photography and development also. The dot percentage measurement can be carried out with the aforementioned conventional measuring device; however, the conventional measuring device is not suitable for frequently performing the measurement for the following reasons: Since the light measuring section of the conventional device is provided at the lower portion of the case thereof, the light measuring section is out of the operator's field of vision, which makes it difficult to place the light measuring section at a portion to be measured of an object. A film density may be measured by performing the positioning only once; however, in measuring a dot percentage as described above, the operator has to assume an uncomfortable position to direct the light measuring section to the portion to be measured. This is undoubtedly troublesome for the operator.

Two practical methods of measuring a dot percentage have been known in the art. In the first method, the shading of a dot film is converted into an electrical signal by means of, for instance, a vidicon to measure the area of a portion of the film where the density is higher than a predetermined value, thereby to measure the dot percentage. In the second method, the light transmittance of a portion to be measured of the dot film is measured to obtain the dot percentage. The first method is advantageous in that it is not affected by fringes around dots and therefore its measurement can be achieved theoretically with high accuracy; however, it is disadvantageous in that the measuring device is bulky and expensive, and therefore not practical. The second method is also disadvantageous in that it is greatly affected by the fringes, and therefore errors are liable to be involved in measuring a halftone-photographed film having a large fringe area.

In general, the error due to the fringe is small or zero with dot percentages of about 0% and about 100% and great with a dot percentage of about 50%. In order to correct this error, in the second method, the multiplying factor of the display section is finely adjusted, or transmission light to be measured is subjected to photoelectric conversion, and then the amplification factor of the resultant electrical signal is finely adjusted. In this correction method, a film having a known dot percentage, preferably about 5%, is prepared, and the fine adjustment is carried out so that the measurement value of the film coincides with the known value. With the film subjected to this correction, the errors due to the fringe are relatively satisfactorily corrected with dot percentages of about 0% and about 100%, but they are still large with a dot percentage of about 50%, as indicated in FIG. 2. The relation of the dot percentage to the light transmittance is not linear because of the influence of fringes, that is, it is expressed by a characteristic curve which is curved in the vicinity of 50% as shown in FIGS. 3 and 4. Nevertheless, the conventional correction method assumes that the relation of the dot percentage to the light transmittance is linear, and performs fine adjustment of this straight line slope. Accordingly, in the conventional correction method, a relatively great error remains in the vicinity of 50% when referred to the errors at dot percentages 0% and 100%.

When a dot film is subjected to reduction by using an iron chelate group reducer, its portion subjected to the reduction is colored yellow-brown. When this film is measured in the second method the light transmittance is affected by the colored portion, and the measured dot percentage involves errors. These errors depend on the amount of reduction, and therefore the correction cannot be achieved by the measuring device according to the second method.

SUMMARY OF THE INVENTION

Accordingly, a first object of this invention is to readily and quickly measure the dot percentage of a dot film by forming a light receiving section and a display section as one unit.

A second object of the invention is to display the amount of reduction of a dot film as well as the dot percentage thereof by simple operation.

A third object of the invention is to obtain a correct dot percentage and a correct amount of reduction by simple operation thereby to improve work efficiency in printing process.

A fourth object of the invention is to correct the effect of fringes on a dot film with respect to light transmittance, thereby to obtain a measurement value with high accuracy.

A fifth object of the invention is to provide a correction circuit simple in construction.

The foregoing objects and other objects as well as the characteristic features of the present invention will become more apparent from the following detailed description and the appended claims when read in conjunction with the accompanying drawings.

BRIEF DESCRIPTION OF THE DRAWINGS

In the accompanying drawings:

The part (A) of FIG. 1 is an explanatory diagram showing a conventional dot percentage measuring device;

Figure 4:
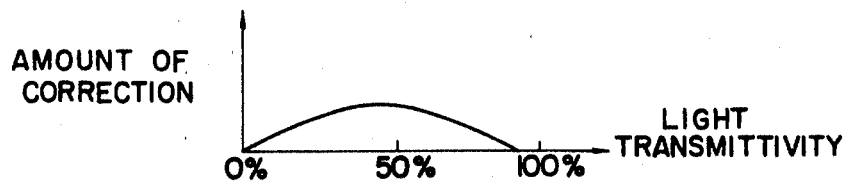
Figure 5:
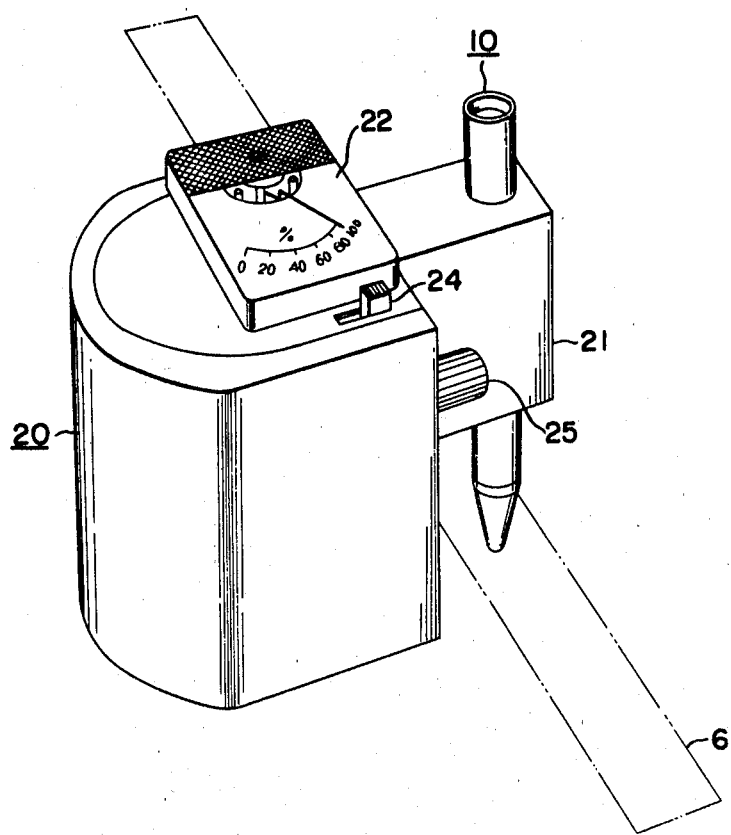
Figure 6:
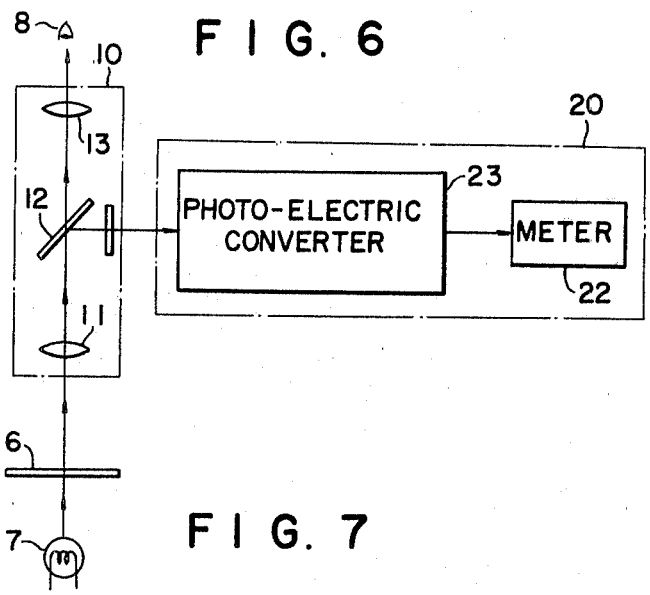
Figure 7:
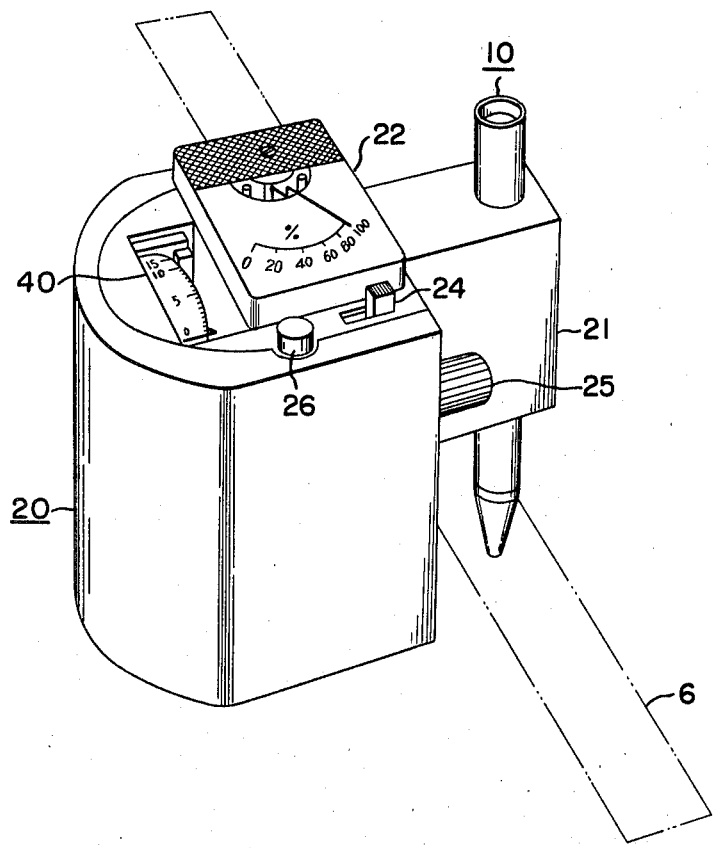
Figure 8:
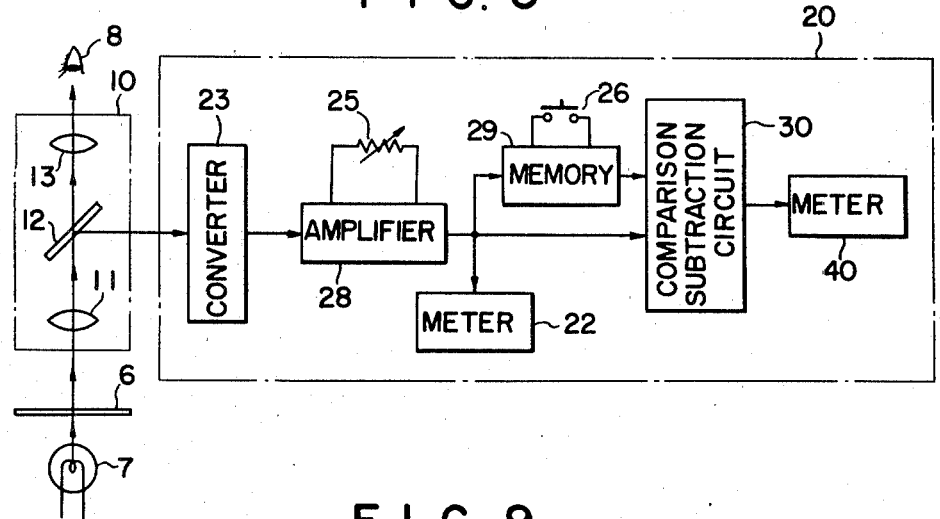
Figure 9:
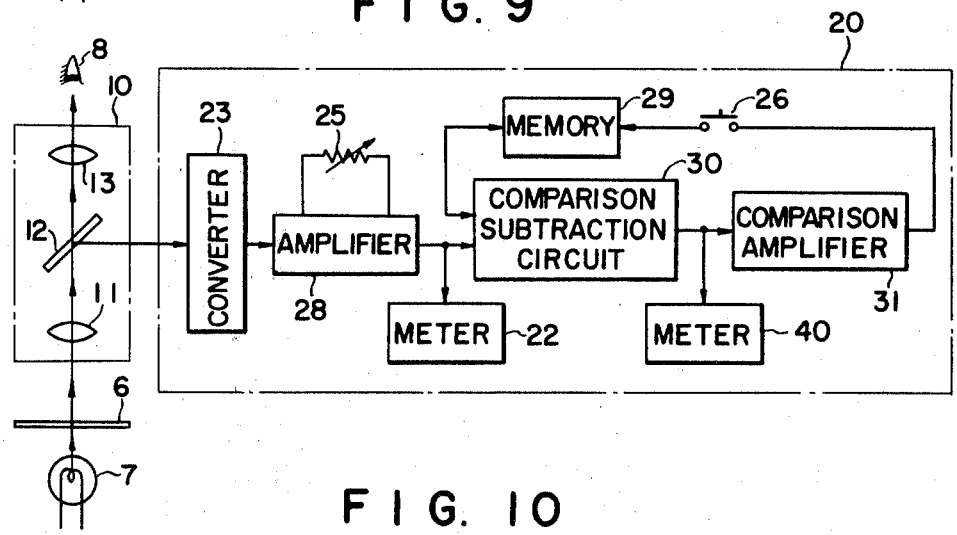
Figure 10:
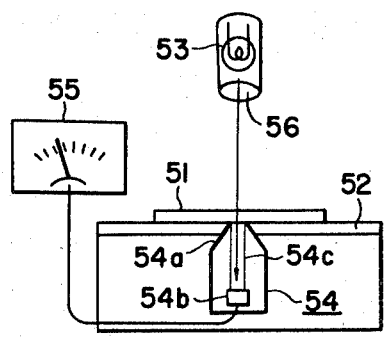
Figure 11:
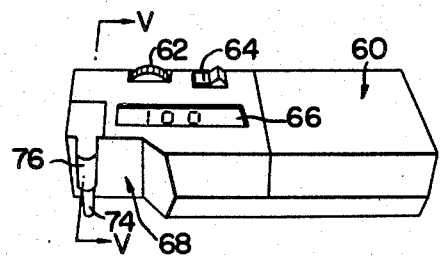
Figure 15:
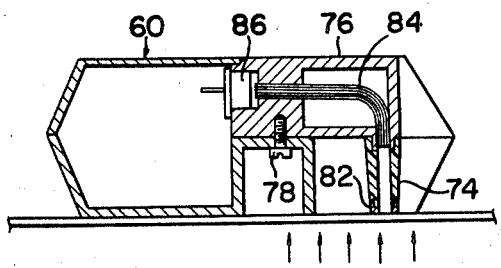
Figure 16A:
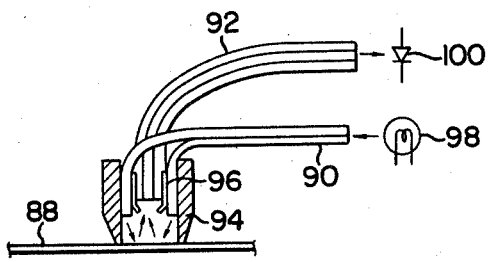
Figure 16B:
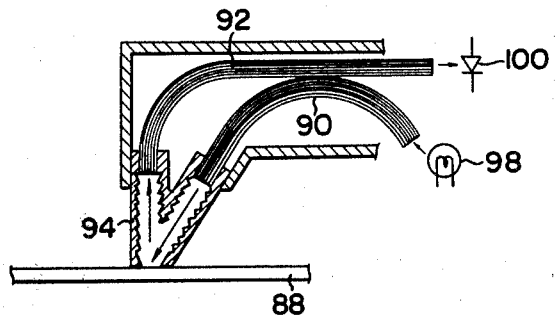
Figure 16C:
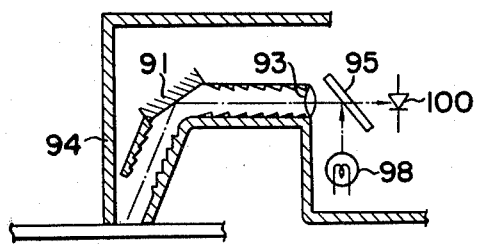
Figure 20:
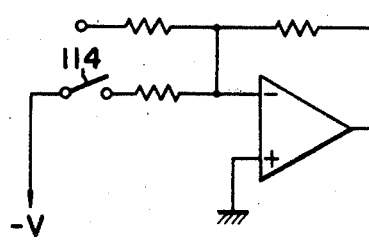
Figure 21:
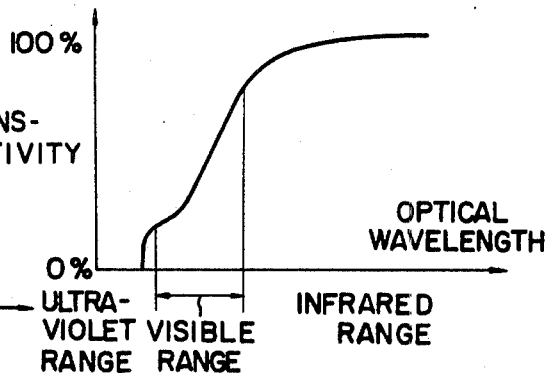
Figure 26:
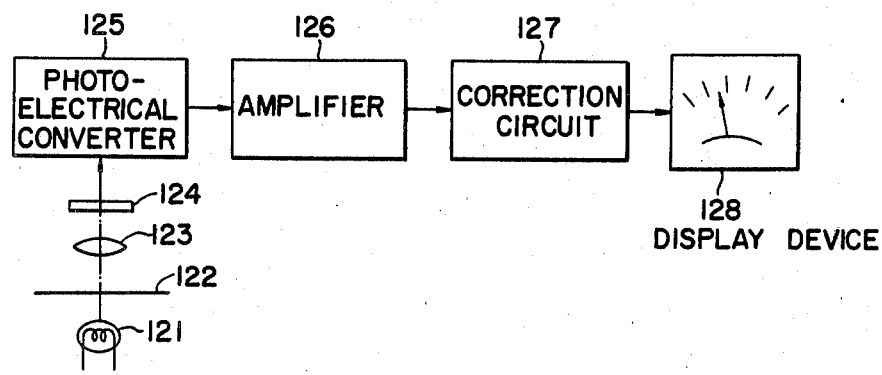
Figure 27:
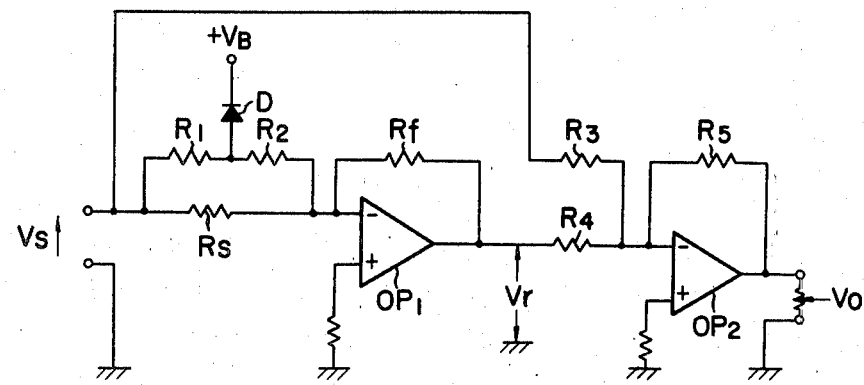
Figure 28:
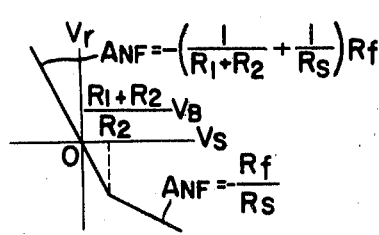
Figure 29:
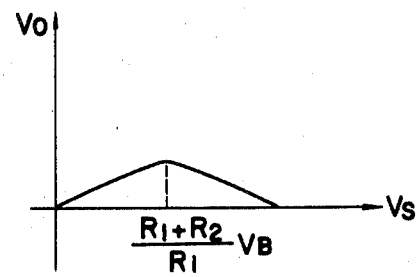
Figure 30:
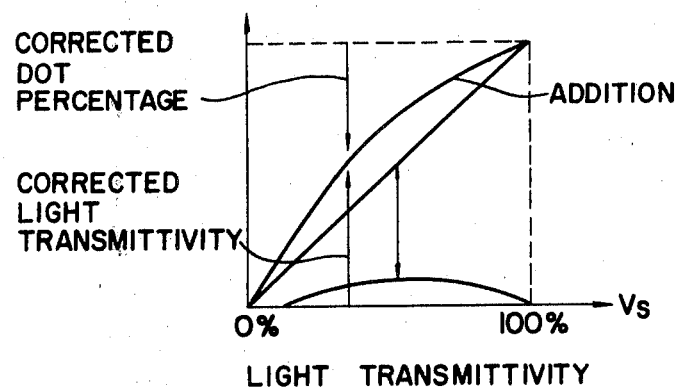
Figure 31:
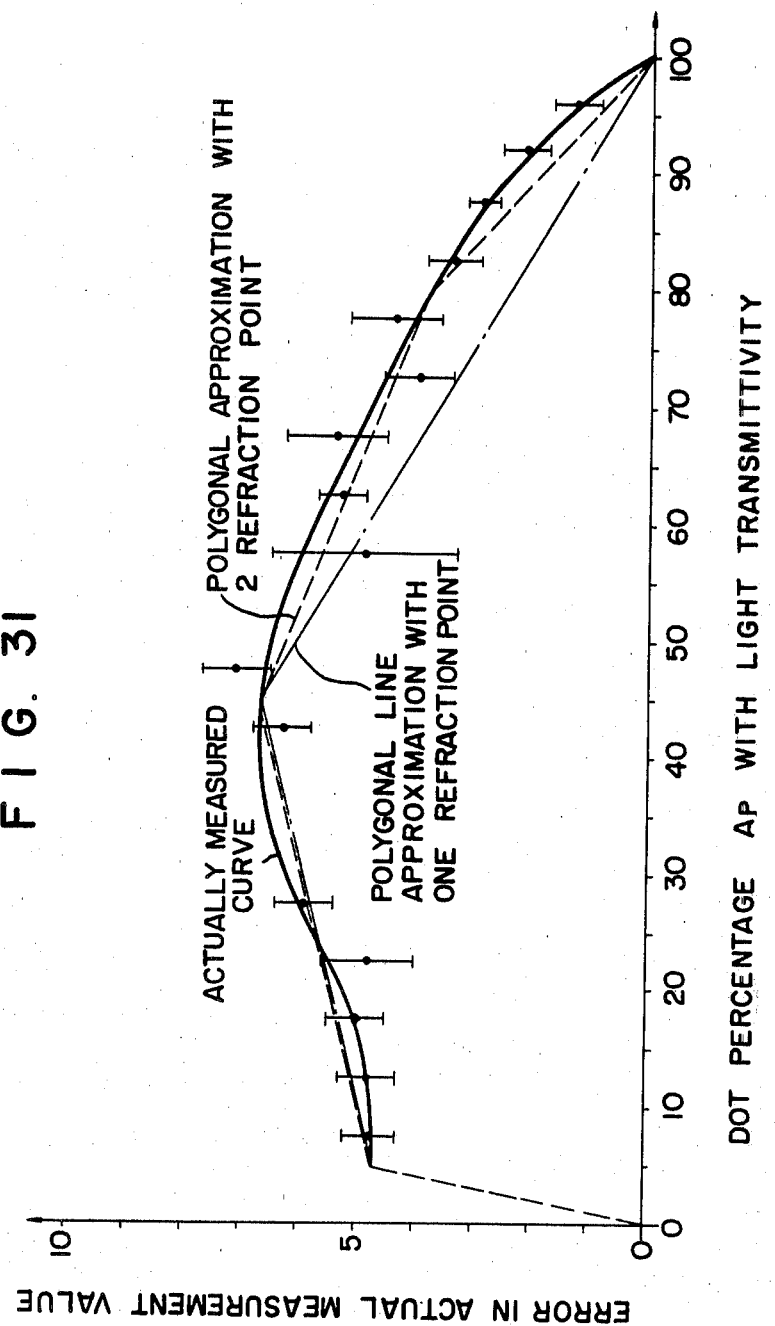

The part (B) of FIG. 1 is also an explanatory diagram for a description of the operation of the measuring device shown in the part (A) of FIG. 1;

FIG. 2 is a graphical representation indicating measurement values obtained according to a conventional correction method;

FIG. 3 and FIG. 4 are graphical representations illustrating the transmittance error versus the amount of correction;

FIG. 5 is a perspective view showing one example of a dot percentage measuring device according to this invention;

FIG. 6 is an explanatory diagram, partly as a block diagram, showing the internal arrangement of the measuring device shown in FIG. 5;

FIG. 7 is a perspective view showing another example of the dot percentage measuring device according to the invention, in which a reduction amount indicating device is additionally provided;

FIG. 8 and FIG. 9 are explanatory diagrams showing examples of the internal arrangement of the measuring device shown in FIG. 7, respectively;

FIG. 10 is an explanatory diagram showing another example of the dot percentage measuring device according to the invention;

FIGS. 11 through 14 are perspective views showing various examples of the measuring device according to the invention;

FIG. 15 is a sectional view taken along line V—V in FIG. 11;

FIGS. 16(A), 16(B) and 16(C) are vertical sectional views showing different examples of a light receiving cylinder;

FIGS. 17 and 18 are sectional views showing modifications of a light receiving cylinder in FIG. 11;

FIG. 19 is a block diagram showing a signal processing circuit;

FIG. 20 shows a positive and negative switching circuit;

FIG. 21 is a plot of optical wave-length versus light transmittance;

FIGS. 22 through 25 are diagrams useful in describing a correction principle according to this invention;

FIG. 26 is an explanatory diagram showing another example of the measuring device according to the invention;

FIG. 27 is a circuit diagram showing the correction circuit portion of the measuring device shown in FIG. 26;

FIG. 28 through FIG. 30 are graphical representations useful in describing the operation of the measuring device shown in FIG. 26;

FIG. 31 is a plot of the actual measurement values versus dot percentages having known light transmittances.

Figure 32:
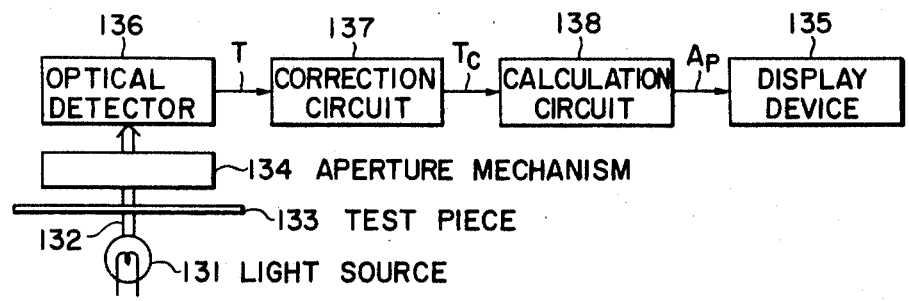
Figure 33:
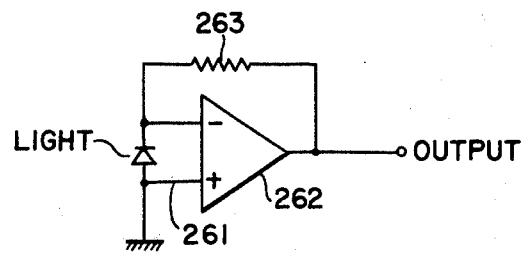
Figure 34:
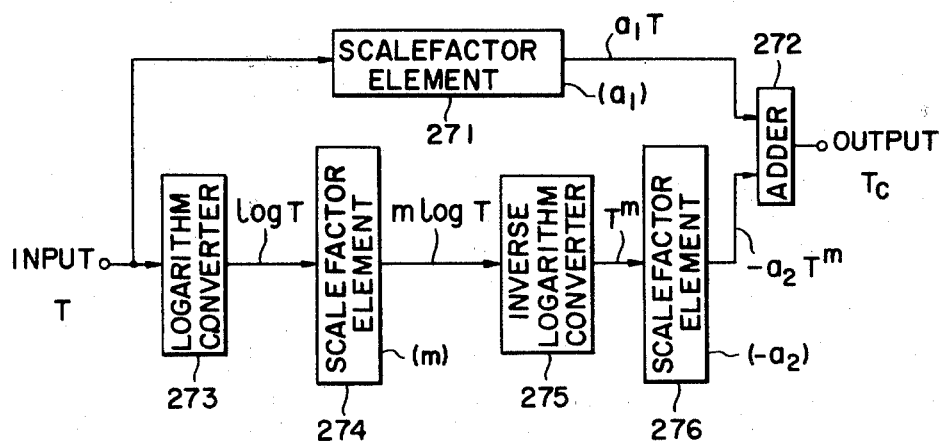
Figure 37:
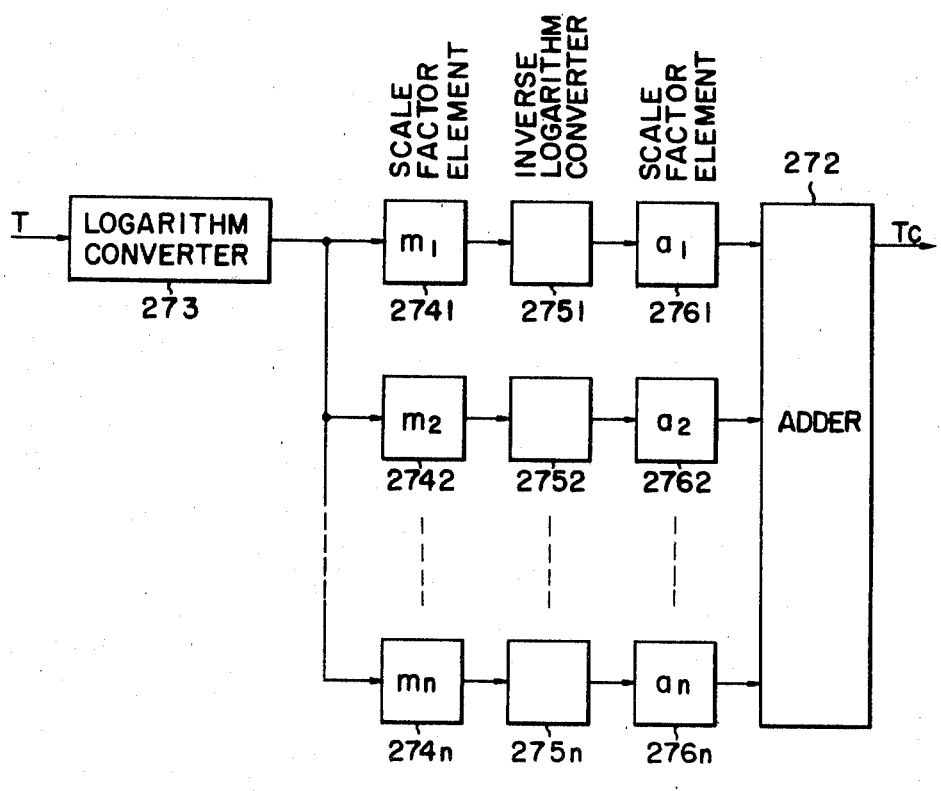
Figure 38:
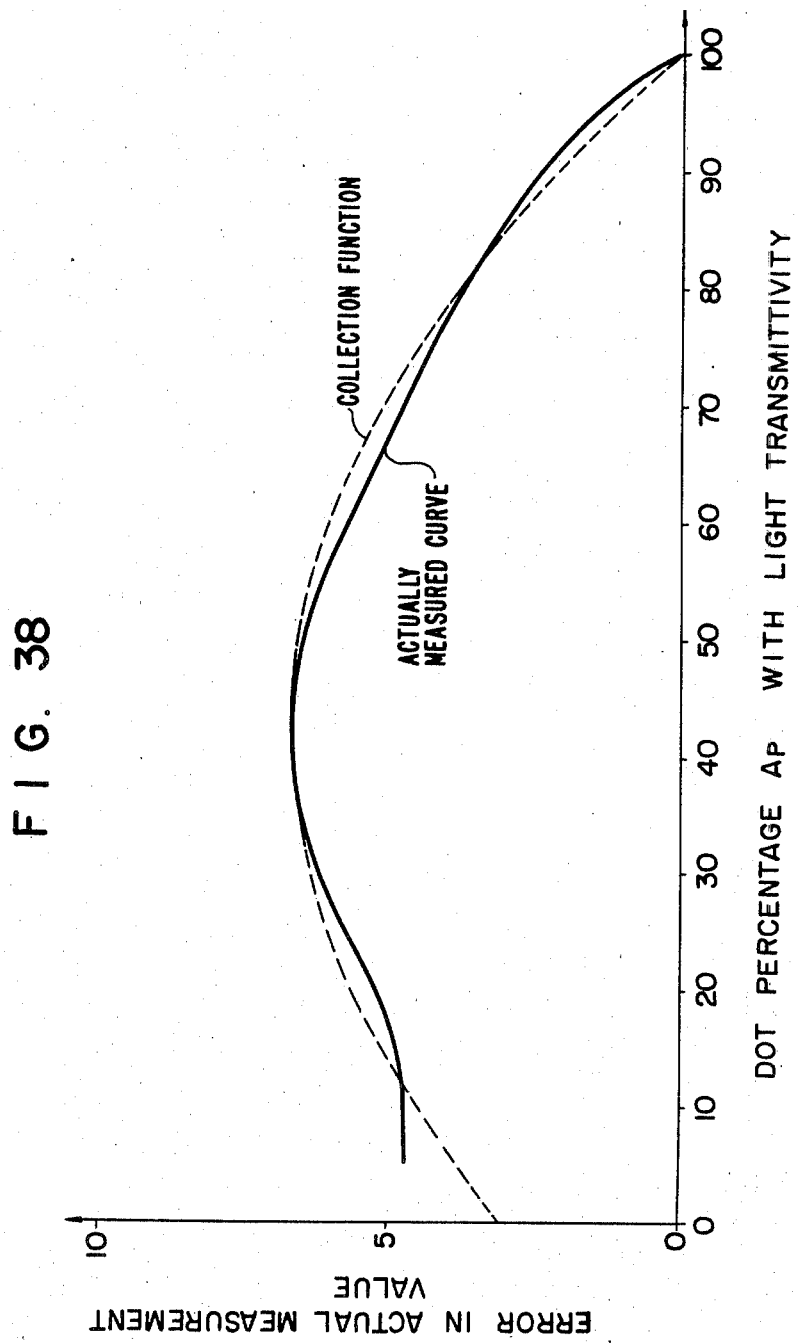
Figure 39:
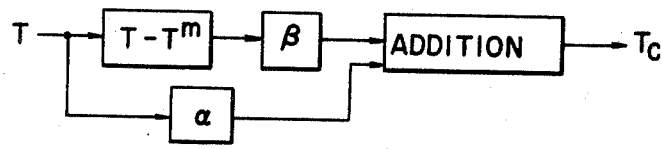
Figure 40:
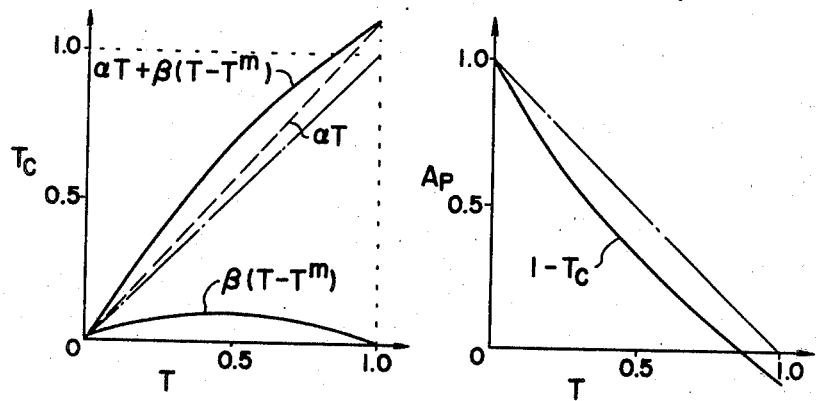
Figure 41:
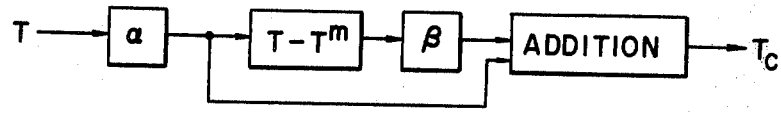
Figure 42:
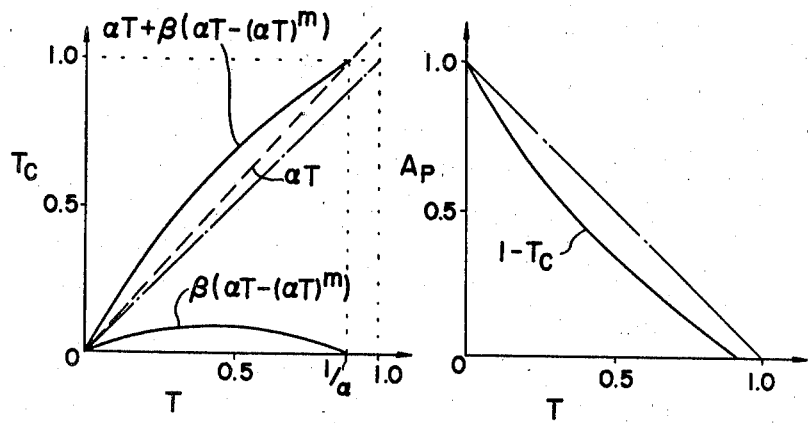

FIG. 32 is an explanatory diagram showing another example of the measuring device according to the invention;

FIG. 33 is a circuit diagram showing one example of an optical detector employed in the measuring device shown in FIG. 32;

FIG. 34 is a block diagram showing one example of a correction circuit employed in the present invention;

FIG. 35 and FIG. 36 are explanatory diagrams showing other examples of the measuring device according to the invention;

FIG. 37 is a block diagram showing another example of the correction circuit employed in the invention;

FIG. 38 is a graphical representation indicating relaionships between dot percentages and errors in actual measurement value in the correction circuit shown in FIG. 37;

FIG. 39 and FIG. 41 are block diagrams showing other examples of the correction circuit employed in the invention, respectively; and FIG. 40 and FIG. 42 are graphical representations showing the correction characteristics of the correction circuits shown in FIGS. 39 and 41, respectively.

DETAILED DESCRIPTION OF THE INVENTION

A first example of a dot percentage measuring device according to this invention, as shown in FIG. 5, comprises an elongated microscope section 10 to observe a test piece with dots 6 from above, and semi-cylindrical dot percentage displaying section 20 which holds the middle portion of the microscope section 10 and displays a dot percentage on a meter 22 graduated in equal increments. A power switch 24 and the zero-adjustment knob 25 of the meter 22 are provided on the outer wall of the dot percentage displaying section 20. The internal arrangement of the device is as shown in FIG. 6. More specifically, the microscope section 10 comprises an objective lens 11, a half-mirror 12, and an eye-piece 13. The dot percentage displaying section is made up of a photo-electric converter 23 adapted to convert the quantity of light reflected by the half-mirror 12 into an electrical data, and the meter adapted to indicate the electrical data on its scale graduated in equal increment. In observing the sample, the test piece 6 is irradiated by a lamp 7 or a natural light.

If the dots on the test piece 6 are subjected to reduction by using a reducer, portions around the dots are stained, causing erroneous measurement, because it is difficult for light from the lamp 7 to pass through the portion thus stained, that is, the portions allow light to pass therethrough in printing on a printing plate and form no dots.

During the development of the device, the inventor has found that light having wavelength in an infrared ray range can pass through the stained portions, but visible light and ultraviolet light cannot pass therethrough.

Therefore, it is desirable that the half-mirror 12 of the microscope section 10 is made up of an interference filter which reflects the infrared light toward the photo-electric converter 23 and permits the visible light or the like to pass therethrough so that it is directed toward the eye-piece 13. An infrared ray passing filter may be disposed on an optical path extended from the half-mirror 12 to the photo-electrical converter. It is preferable that the photo-electric converter 23 has an element such as silicon photo-diode which receives infrared rays satisfactorily. The lamp 7 may be of an infrared ray source; however, this is not recommended because it is difficult to perform visual inspection.

In operation, the power switch 24 (FIG. 5) is turned on and the test piece 6 (FIG. 6) is disposed in place below the microscope section 10. Light passed through the test piece 6 enters the objective lens 11, and a part (which can be either visible light or ultraviolet light) of the output light of the objective lens reaches the eye-piece 13, whereby the observer 8 can evaluate the configuration of the dots on the test piece 6. A part of the output light of the objective lens 11 is reflected in a perpendicular direction by the half-mirror 12 to enter the photo-electrical converter 23 where it is converted into an electrical data corresponding to the input light quantity. The electrical data is indicated by the meter 22 (such as a voltmeter). As the light passed through the test piece is proportional to the dot percentage, the value indicated by the meter 22 is proportional to the dot percentage. For instance, if the test piece 6 is completely black, the meter indicates 100%, and if the test piece is transparent, it indicates 0%. Percentage indication on the meter 22 can be adjusted by the zero-adjustment knob 25 according to the quantity of light of the light source or the optical transmittivity of a film form the test piece.

As shown in FIG. 7, another example of the dot percentage measuring device is provided with a reduction amount indicating device. In this case, a memory switch 26 is provided which temporarily stores a dot percentage and is operated in obtaining the amount of reduction. The internal arrangement of the device thus organized is as shown in FIG. 8. Its microscope section 10 has an optical system made up of an objective lens 11, a half-mirror 12 and an eye-piece 13. Its dot percentage indicating section 20 comprises a photo-electrical converter 23 for converting light reflected by the half-mirror 12 into electrical data, an amplifier circuit 28 for amplifying the electrical data from the photo-electrical converter 23, a meter 22 for indicating the output of the amplifier circuit 28 on its scale graduated in equal increments, a memory circuit 29 for storing the output of the amplifier 28 upon operation of the memory switch 26, a comparison/subtraction circuit for subjecting the value stored in the memory circuit 29 and the output value of the amplifier circuit 28 to comparison and subtraction thereby to obtain a dot reduction figure, and a meter 40 for indicating the output of the comparison/subtraction circuit as either a reduction figure or a dot percentage change.

In operation, the power switch 24 is turned on, and the test piece 6 is disposed in place below the microscope section 10. Light passed through the test piece 6 enters the objective lens 11, and a part (which can be either visible light or ultraviolet light) of the output light of the objective lens reaches the eye-piece 13, whereby the observer 8 can evaluate the configuration of the dots on the test piece 6. A part of the output light of the objective lens 11 is reflected in a perpendicular direction by the half-mirror 12 to enter the photo-electrical converter 23 wher it is converted into an electrical signal corresponding to the input light quantity. The electrical signal is amplified by the amplifier circuit 28. The electrical signal thus amplified is indicated on the meter 22 (such as a voltmeter). Since the light passed through the test piece is proportion to the dot percentage, the value indicated by the meter 22 is proportional to the dot percentage.

The output of the amplifier circuit 28 is applied to the memory circuit 29 and the comparison/subtraction circuit 30; however the output of the memory circuit 29 is equal to the input thereof when the memory switch 26 is not operated. Accordingly, the same signals are applied to the comparison/subtraction circuit 30, and therefore the output of the comparison/subtraction circuit 30 is zero, which is indicated on the meter 40. If the memory switch 26 is depressed, the memory circuit 29 stores the output value of the amplifier circuit 28. As the dot percentage is varied by moving the test piece 6 or replacing it with another one, the amount of light passing through the test piece 6 is varied and the output of the amplifier circuit 28 is also varied. In this operation, as the output value of the memory circuit 29 is maintained unchanged, the inputs to the comparison/subtraction circuit 30 are different in level from each other, and therefore an output signal corresponding to the difference is provided by the circuit 30 and is indicated by the meter 40.

Thus, with the dot percentage measuring device, the configuration of the dots can be observed using the microscope section and the dot percentage can be indicated by the meter. Furthermore, the dot reduction increment or the dot increment increment can be indicated by the meter. This will facilitate improvement of off-set retouching process. The memory circuit 29 is cleared by depressing the memory switch again.

Another example of the dot percentage measuring device according to the invention will be described with reference to FIG. 9 in which those components which have been previously described with reference to FIG. 8 have therefore been similarly numbered. In this example, the output of the comparison/subtraction circuit 30 is applied to a comparison amplifier 31 where it is amplified and is then applied to the memory circuit 29. When the memory switch 26 is not operated (depressed), the input to the memory circuit 29 is applied, as it is, to the comparison/subtraction circuit 30. Therefore, if two inputs to the comparison/subtraction circuit 30 are different in level, a signal corresponding to the difference is outputted by the circuit 30 to be applied to the meter 40. Thus, the difference between the output of the memory circuit 29 and the output of the amplifier circuit 28 is indicated on the meter.

Next, the memory switch 26 is depressed to connect the output of the comparison amplifier 31 to the memory circuit 29. If in this case two inputs to the comparison/subtraction circuit 30 are different in level from each other, a signal corresponding to this difference is outputted by the comparison/subtraction circuit 30 to be applied to the comparison amplifier 31, in response to this output signal the comparison amplifier 31 outputs a signal so that the two inputs become equal to each other. If under this condition the memory switch 26 is depressed, then the output signal of the memory circuit 29 coincides with the output of the amplifier circuit 28. If the memory circuit is opened, the output signal of the comparison amplifier 31 is not applied to the memory circuit, and therefore the memory circuit 29 holds the output signal value obtained when the switch 26 is opened.

Similarly as in the above-described case, as the dot percentage is changed, the output of the amplifier circuit 28 is also changed. As a result, the two inputs to the comparison/subtraction circuit 30 become different from each other, and a signal corresponding to this difference is provided, and is indicated as the reduction data or the increment data by the meter 40. Thus, the same effect 25 before can be obtained by this example of the dot percentage measuring device.

Another example of the dot percentage measuring device according to the invention, as shown in FIG. 10, comprises: a light receiving section 54 provided inside a measuring table 52; and a stationary light emitting section 53 provided above the light receiving section 54 in such a manner that the former 53 confronts the latter 54. The light receiving section 54 is made up of a cylindrical head 54a having an opening at one end, a light receiving element 54b such as a photo-electrical conversion element for receiving light from an object 51 to be measured (hereinafter referred to as a test piece 51 when applicable), a pipe 54c for introducing light through the opening to the light receiving element 54b. The light receiving section 54 is arranged so that the upper edge of the opening of the head 54a and accordingly of the pipe 54c is flush with the upper surface of the measuring table 52. Accordingly, if the test piece 51 is placed on the measuring table 52, then the lower surface of the test piece 51 is in close contact with the upper edge of the opening of the head and the pipe 54c. The light receiving element 54b is electrically connected to a display section 55 so that the quantity of light passed through the test piece 51 is received by the light receiving element 54b and displayed by the display section 55.

In measuring the dot percentage of a test piece 51, the test piece 51 is positioned suitably on the opening of the head 54a and the pipe 54c. Then, light having a predetermined intensity is applied to the test piece 51 through a condenser lens 56 provided on the outlet of the light emitting section 53, so that the light receiving element 54b in the light receiving section 54 can receive light passed through the test piece 51. The quantity of light received by the light receiving element 54b is indicated on the display section 55. Since both the light emitting section 53 and the test piece 51 are exposed outside, the measurement is liable to be affected by external light. In order to eliminate this difficulty, light other than visible light, that is, infrared light (or ultraviolet light) is employed as the light emitted by the light emitting section 53, an infrared ray transmitting filter (not shown) is provided in the optical path extending from the test piece 51 to the light receiving element 54b in the light receiving section, and a silicon photo-diode receiving infrared rays is employed as the light receiving element. In this case, it is possible to keep the operator's sense of sight from being affected by the external light. Furthermore, when of using ultraviolet light, it may be necessary to employ a means for eliminating the effect of visible light.

This device shown in FIG. 10 can be incorporated in a washing table used in the reduction process. In this case, after the test piece 51 is subjected to reduction, the amount of reduction can be measured immediately. This will considerably improve the work efficiency.

Shown in FIGS. 11 through 14 are other different examples of the dot percentage measuring device according to the invention. Each device is light and small so that it can be readily operated or handled by and carried with the operator. These devices can measure not only a dot percentage but also a dot density. Each device comprises: a case 60 made up of the upper and lower halves which can be separated from each other when required; a zero-adjustment dial 62 exposed outside the case 60; a power switch 64, and a measured value displaying window 66. A recess 68 (70 or 72) is formed in one portion of the wall of the case. Cantilevered by a supporting arm 76 in the recess is a light receiving cylinder 74 which receives light reflected by and passed through a test piece.

The term "test piece" as used herein is intended to mean an object to be measured having an image formed with dots or an image of continuous tone, such as a screen negative film, a screen positive film, printed material, photographing film or the like.

In the example shown in FIG. 11, the recess 68 is formed at one corner of the case 60. The light receiving cylinder 74 and the supporting arm 76 are provided within the area of the recess 68, which is defined by extending the side walls of the case. In this example, the supporting arm and the light receiving cylinder are so designed as to introduce light passed through the test piece; however, they may be so designed as to introduce light reflected by the test piece as shown in FIG. 16(A). However, it is necessary that the mounting angles of the light source and the light receiving section are such that regular reflection light is not received. An arrangement meeting this requirement is shown in FIG. 16(B).

In this case, the test piece 88 is an opaque printed material. Optical fibers are divided into two bundles 90 and 92 by a holding member 96 in a light receiving cylinder 94. One 90 the bundles of optical fibers is directed to a light source 98 and the other 92 is directed to a light receiving element 100.

A reflecting mirror, a prism, or a half-mirror (or the like) instead of the optical fibers may be employed as the light receiving means. FIG. 16(C) shows a case where a reflecting mirror and a half-mirror are used in combination. In FIG. 16(C), reference numerals 91, 93 and 95 designate the mirror, a lens, and the half-mirror, respectively.

The above-described light receiving cylinder 74 or 94 may be supported as illustrated in FIG. 17 or 18. The construction shown in FIG. 17 or 18 is intended to absorb mechanical shocks which may be applied to the light receiving cylinder during measurement.

In the arrangement shown in FIG. 17, the afore-mentioned supporting arm 76 is replaced by a shock absorber 102 such as a spring or a rubber block (not shown).

In the case of FIG. 18, the supporting arm 76, the light receiving cylinder 74 and a part of the upper half of the case are formed as one unit. The part of the upper half of the case is coupled through a hinge 104 to the other part of the upper half of the case, and a portion, corresponding to the supporting arm, of the one unit is coupled to the lower half of the case with a screw 106 through an elastic member 102 such as a spring.

Figure 12:
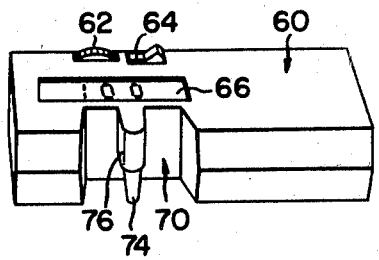

In the example shown in FIG. 12, the recess 70 is formed in the middle portion of a side wall of the case, and the light receiving cylinder 74 is held as shown in FIG. 15, 17 or 18. In this case also, the light receiving cylinder 74 is positioned inwardly of the side wall or to be flush with the side wall. It is difficult for the operator's hand or the like to gain access to the light receiving cylinder when compared with the light receiving cylinder in FIG. 11, and therefore the light receiving cylinder is less subject to damage. However, it should be noted that as the recess is formed at the corner of the case in the case of FIG. 11, the operator can readily hold it in his hand.

Figure 13:
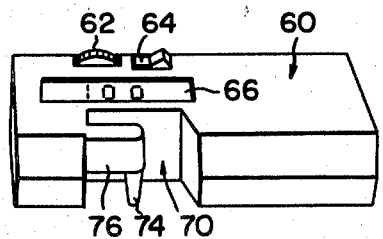

The recess 70 in FIG. 13 has the same shape as the recess in FIG. 12, but the supporting arm in FIG. 13 protrudes from a side wall of the recess. This arrangement is employed when it is convenient in association with an electrical circuit incorporated in the measuring device.

Figure 14:
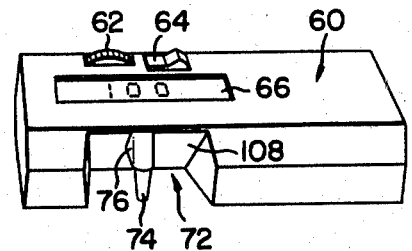

In the case of FIG. 14, the recess 72 is formed in such a manner that it extends from the side wall of the case to the bottom wall. In this point, the recess 72 in FIG. 14 is different from the recess 68 or 70 which extends from the top wall of the case to the bottom wall.

In the example of FIG. 14, as the light receiving cylinder 74 is provided below the slant wall of the recess 72, it is rather difficult to see the test piece when compared with the above described examples. However, the light receiving cylinder 74 is more satisfactorily protected from damage being covered by the top wall and the side walls.

The operation of each measuring device shown in FIGS. 11, 12, 13 and 14, will be described with reference to a signal processing circuit shown in FIGS. 19 and 20.

When, light passed through a transparent film 80 such as a screen positive film is utilized in measuring a dot percentage, a measuring position is specified by marking desired points of a light table 110 with round points 112 or the like in order to eliminate the occurrence of a measurement error due to the fluctuation in light intensity of the light table 110 on which the film is placed. Then, a portion having a dot percentage 0% of the test piece 80 is placed between the marks 112.

The power switch 64 (FIGS. 11-14) is turned on, and the zero-adjustment dial 62 is operated so that a digital display section 66 is set to zero (0).

Then, a portion to be measured of the test piece 80 (FIG. 1(A)) is placed between the marks 112, and the measuring device is placed on the portion so that the light receiving cylinder 74 confronts that portion. Thereafter, the operator reads a dot percentage indicated on the display section 66. Measurement of the dot percentage is carried out for various portions of the film and is recorded. If the resultant data is greater than a predetermined value, it is subjected to reduction process so that the dot percentage is reduced. If the resultant value is smaller than the predetermined value, photographing is carried out again.

On the other hand, in the case of density measurement, the zero-adjustment is performed directly on the light table and between the marks, and then a portion to be measured of the test piece is placed between the marks for measurement.

In the case where the test piece 88 is an opaque printed material, the test piece is placed on a flat surface other than the light table, and the measurement is performed with the measuring device having the light receiving cylinder 94 shown in FIG. 16 similarly as in the above-described measurement.

Referring to FIG. 19, a DC component extracting filter is a circuit for eliminating light flickering due to AC power supply to improve the measurement accuracy. A switch 114 is provided in a circuit as shown in FIG. 20, so as to read negative and positive values. If the switch 114 is turned on, a positive dot percent or density is displayed, and if it is turned off, a negative dot percent or density is displayed.

An electric source 116 is a battery incorporated in the case; however, it may be provided outside the case so that it is connected through a cord to the measuring device.

If a dot percentage is measured, a dot density can be calculated from the dot percentage. In contrast, if a dot density is measured, a dot percentage can be calculated from the dot density.

Factors causing errors in dot percentage measurement using light transmittance may be the decrease in light transmittance due to the yellow-brown created by the reduction process. The decrease in light transmittivity due to fringe is substantially constant if the conditions of halftone photography and development are constant, and it can be corrected with a predetermined value. However, as the light transmittivity is further decreased by reduction, it has been difficult to accurately correct the light transmittivity of a halftone film subjected to reduction. The result of measuring the spectral light transmittivity of a portion which has been colored brown by reduction with a iron chelate group reducer is as indicated in FIG. 21. As is apparent from FIG. 21, the spectral light transmittivity is such that light in the ultraviolet ray range scarcely passes through the brown portion, the transmittivity of light in the visible ray range is abruptly increase, and the transmittivity of light in the infrared ray range is more than 80%. Accordingly, the dot percentage measurement with light in the ultraviolet ray range or the visible ray range is greatly affected by the portion colored by reduction. However, the dot percentage measurement with light in the infrared ray range is less affected by such a portion. This will become more apparent from FIGS. 22, 23, 24 and 25.

Figure 22:
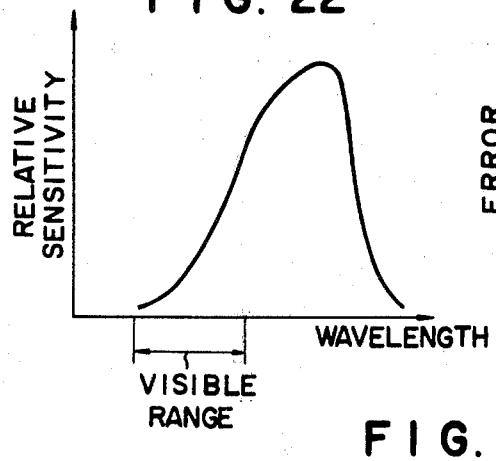
Figure 23:
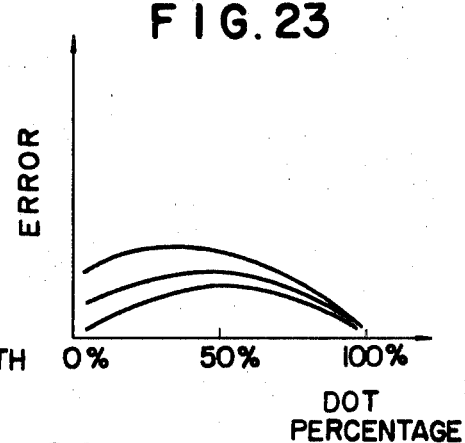
Figure 24:
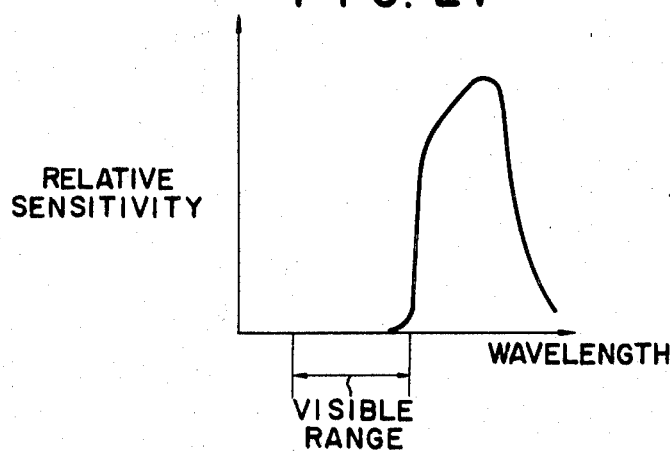
Figure 25:
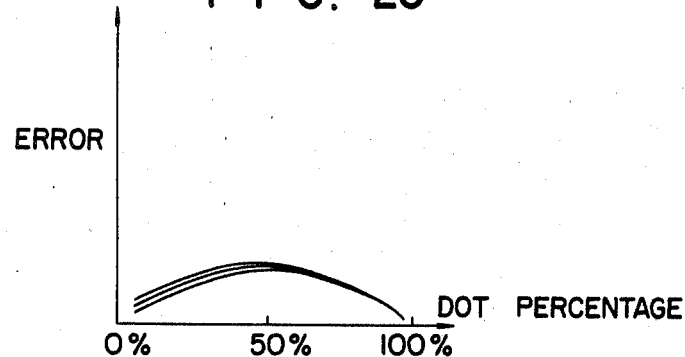

A first instance is shown in FIGS. 22 and 23, in which an iodine lamp is employed as the light source, and a silicon photo-diode is used as the light receiving section. A second instance is shown in FIGS. 24 and 25, in which in addition to the components employed in the first instance an optical filter for cutting off the light in the ultraviolet ray range and the light in the visible ray range is additionally provided. Each of the FIGS. 22 and 24 indicates the relative sensitivity characteristic of the detecting section with respect to the wavelength of transmitted light. Each of the FIGS. 23 and 25 indicates the characteristic of an error caused by reduction. As is clear from these graphical representations, the first instance is most sensitive to the light in the infrared ray range and is also sensitive to the visible light. Therefore, the first instance is affected by the portion colored by reduction process, and accordingly, the measurement error is increased as the amount of reduction is increased. In the second instance, the optical filter is added to the first instance so as to decrease the sensitivity of the detecting section to the ultraviolet light and the visible light. In the case of the second instance, the dot percentage measurement is scarcely affected by the portion colored by reduction process, and the increment of the measurement error due to the increase of the amount of reduction is suppressed as shown in FIG. 25. The same effect can be also obtained by using a light source which does not emit ultraviolet light and visible light. Thus, if, after the influence of the reduction is eliminated to stabilize the amount of error, a function having a characteristic as shown in FIG. 4 (the characteristic being such that the light transmittivity is small or zero at about 0% and 100%, and is maximal at about 50%) is generated to be added, as correction data, to the light transmittance or data related thereto. As a result the dot percentage can be obtained with high accuracy.

The arrangement of a device performing such an operation as described above is as shown in FIG. 26.

In the device shown in FIG. 26, light from a light surce 121 passes through a test piece 122, and is introduced through a lens system 123 and a filter 124 to a photo-electrical converter 125, whose output is an electrical signal corresponding to the quantity of light passed through the test piece. As the filter 124 allows only infrared light to pass therethrough, the influence of reduction can be eliminated. The output of the photoelectrical converter 125 is amplified to the operating level of a correction circuit 127 connected thereto. After the above-described correction is carried out, the dot percentage is displayed on a display device 128. Where an AC light source is used as the light source 121, it is preferable to insert a circuit (not shown) adapted to prevent light flickering between the amplifier 126 and the correction circuit 127.

In general, the amount of fringe is substantially constant if the conditions of halftone photography and development are fixed. Therefore, the influence of fringe can be corrected by presetting the correction signal. Such a correction signal can be obtained by adding the signal shown in FIG. 4 to the electrical signal proportional to the light transmittance.

A circuit for generating the above-described correction signal, as shown in FIG. 27, is made up of operational amplifiers OP1 and OP2, a diode D and resistors R1 through R5. The output Vr of the operational amplifier OP1 is changed in amplification factor at the input voltage $(R1+R2)/(R2) V_B$ as shown in FIG. 28, that is its characteristic curve is as a polygonal line. If the voltage Vr having such a characteristic and the input voltage Vs is subjected to addition in a suitable ratio in the operational amplifier OP2, then a signal approximating the amount of correction can be obtained as indicated in FIG. 29. That is, if the input voltage Vs is employed as an electrical signal proportional to the light transmittivity, $V_D$ may be employed as an electrical signal approximating the amount of correction for the light transmittivity (FIG. 4).

If this correction signal is added in a suitable ratio to the signal proportional to the light transmittivity as shown in FIG. 30, then the value of light transmittivity in the vicinity of 50% can be corrected as desired without affecting the values at 0% and 100%. The value $V_O$ is the aforementioned amount of correction to be preset.

FIG. 31 shows an actually measured curve to indicate what errors the dot percentage measurement utilizing light transmittivity include. That is, the curve is obtained by averaging the test results of about thirty samples. The amount of error is defined as follows: A measurement value obtained according to the above-described method is employed as a reference value. The amount of deviation of a value calculated from Equation $Ap = (1-T) \times 100\%$ (where Ap is the dot percentage, and T is the light transmittivity) from the reference value is the amount of error. The one-dot chain line indicates a correction function with a polygonal line which has one refraction point so that the amounts of error at dot percentages Ap 5%, 45% and 100% coincide with one another. The correction function indicated by the one-dot chain line includes relatively great errors more than 1% in the vicinity of Ap 70-90%. This error may be reduced by providing the refraction point in the vicinity of Ap 55-60%; however, in this case, an error more than 1% is caused in the vicinity of Ap 35-45%. Therefore, in order to improve the accuracy, it is necessary to increase the number of refraction points. The dotted line in FIG. 31 has an additional refraction point at Ap 80% in order to reduce the erors in the vicinity of Ap 70-90%. That is, the dotted line indicates a polygonal line having two refraction points to approximate the actually measured curve (solid line). However, if the number of refraction points is increased, the number of adjustment points is increased. For instance in the case where two refraction points are provided, as each adjustment point to be set for approximation has to specify three point positions in a plane, six factors are involved, which make the setting of a polygonal line for correction intricate.

As a result of investigation of a number of actually measured value, in the following embodiment of the invention is employed the fact that when the dot percentage of a screen film is measured by using the light transmittivity of the film, a characteristic curve for converting light transmittivity into dot percentage can be relatively readily approximated with a quadratic function with high accuracy.

In this embodiment, it is preferably to use a light source free of flickering and drift in the quantity of light emitted thereby, such as iodine lamp driven by a stable DC source. After passing through a test piece or a halftone film 133, the light emitted by the light source enters an aperture mechanism 134. The aperture mechanism operates to increase or decrease the cross sectional area of the optical path according to the variation in light intensity of the light source 131, thereby to correct a measurement error due to the variation in light intensity of the light source. For instance, in the case of using as the test piece a film having a dot percentage 0%, the aperture mechanism 134 is controlled so that a display device 135 indicates zero. Alternatively, the aperture mechanism may be controlled as follows. That is, by using a film whose dot percentage is known, preferably about 5%, the aperture mechanism is controlled so that the display device 135 shows that dot percentage. An optical detector 136 receives light passed through the aperture mechanism 134 and converts it into an electrical signal T proportional to the quantity of light thus received. A photoelectric tube, a photoconductive element, or a photodiode is employed as the optical detector 136.

FIG. 33 shows one example of the optical detector 136 which is made up of a photodiode 261. The photodiode 261 is connected between the positive and negative input terminals of an operational amplifier 262, and a feedback resistor is connected between the input and output terminals of the operational amplifier 262.

The electrical signal T provided by the optical detector 136 is proportion to the average transmittivity of the measurement portion of the film, and the proportion factor is adjusted by the aperture mechanism 134. The electrical signal T is applied to a correction circuit 137 which operates to correct the measurement error at about 50% which may be caused by the effect of fringe, and an error due to a ghost dot. FIG. 34 is a block diagram showing one example of the correction circuit 137. If in this circuit the input T is represented by an expression ($0 \leq T \leq 1$), then its correction output Tc can be expressed by the following Equation (1):

$$Tc = a_1 T - a_2 T^m \quad (1)$$

After being multiplied by the factor $a_1$ in a scale-factor element 271, the input T is applied to one input terminal of an adder 272. In addition, after being converted into log T in a logarithm converter 273, the input T is multiplied by the factor m in a scale-factor element 274. The output m log T of the scale-factor element 274 is converted into a value $T^m$ by an inverse logarithm converter 275, the output of which is multiplied by the factor $-a_2$ in a scale-factor element 276. The resultant value $-a_2 T^m$ is applied to the other input terminal of the adder 272. As a result, the correction signal Tc in Equation (1) described above is obtained as the output of the adder 272. The signal Tc representative of the correction transmittivity is calculated into an dot percentage Ap by a calculation circuit 138 in accordance with the following Equation (2):

$$Ap = (1 - Tc) \times 100 \quad (2)$$

The signal Ap proportional to the dot percentage of the test piece is displayed as "0%" by a display device 135 when it is zero (0), and as "100%" when 100. Thus, the corrected dot percentage of the test piece 133 can be obtained.

FIG. 35 is a block diagram showing another example of the measuring device according to the invention, in which light emitted by the light source flickers as in the case of a fluorescent lamp in a light table. In order to eliminate the effect of this flickering a DC component extracting filter 139 or a low-pass filter is employed. Thus, the output signal of an optical detector 136 is applied to a correction circuit 137 after its AC components have been removed by the DC component extracting filter 139. In this case, as the output of the correction circuit 137 is not linear to its output, a value obtained by inputting the DC component of a signal including an AC component does not coincide with a signal obtained by inputting the same signal directly to the correction circuit 137. Therefore, it is necessary to provide the DC component extracting filter 139 before the correction circuit 137.

FIG. 36 shows another example of the measuring device in which no aperture mechanism is employed. In this example, it is necessary that the signal is increased or decreased to a predetermined level by performing gain control by a gain control circuit 140 in the front stage of a correction circuit 137, and is then applied to the correction circuit 137. In this case also, as the characteristic of the correction circuit 137 is not linear, the output signal of the correction circuit 137 which is obtained by inputting a signal multiplied by a constant to the correction circuit 137 is different from the value which is obtained by multiplying by the same constant the output of the correction circuit 137 obtained by inputting the signal, as it is, to the correction circuit 137. Therefore, it is necessary to perform the gain control in the front stage of the correction circuit 137. A multi-revolution type variable resistor may be employed in the gain control circuit 140 in FIG. 36. However, this variable resistor is expensive and bulky, and accordingly it is not preferable to employ it in a small measuring device in the view point of a space available. Therefore, in the case of the small measuring device, it is necessary to use a variable resistor which is readily available and can cover all the range with one revolution. However, there is a problem to be solved. That is, in the case of the small measuring device which uses a light table as its light source, its necessary adjustment range is relatively large, three to four times in gain ratio, because the quantity of light from the light table fluctuates greatly. Accordingly, if it is intended to cover all the adjustment range with only one revolution of the small variable resistor, then it is rather difficult to perform fine adjustment. Thus, it is preferable to employ a thread-feed mechanism for the aperture mechanism and to use a multi-revolution type variable resistor with which the fine adjustment can be performed covering all the adjustment range, in the small measuring device.

If the measuring device shown in FIG. 36 is so designed that the gain control circuit 140 is provided with at least two adjustment ranges which are suitably selected by an externally provided change-over switch, then the adjustment can be performed more readily.

The measuring devices shown in FIGS. 32, 35 and 36 have been described with reference to the case where the correction is performed according to Equation (1). However, the accuracy can be increased if the following Equation (3) in which the number of terms is increased is employed:

$$Tc = \sum_{i=1}^{n} a_i T^{m_i} \quad (3)$$

Shown in FIG. 37 is an example of a correction circuit which perform such a function. FIG. 37 will become more apparent when referred to FIG. 34.

An example of such a correction is illustrated in FIG. 38 which may be compared with FIG. 31. In this case, the following correction function is employed:

$$Tc = 1.23T - 0.2T^2 \quad (4)$$

In FIG. 38, an actually measured curve is indicated by the one-dot chain line. The number of factors required to be determined for correction is only three: factors m, $a_1$ and $a_2$; however, the obtained approximation is considerably fine as is apparent from the graphical representation in FIG. 38.

FIG. 39 shows a block diagram of a device adapted to perform the above-described correction, the device being so designed that the adjustment can be readily achieved.

In this method, a signal T representative of a transmittivity which has reached a predetermined level through gain control is multiplied by a factor $\alpha$ to provide a value $\alpha T$, whereby correction as to a base film density and a ghost dot is carried out, and the following function which becomes zero with T=0.1, and maximal with T=0.5 is generated:

$$T - T^m \quad (5)$$

The function is multiplied by a factor $\beta$, and the result is added to the aforementioned $\alpha T$, so as to obtain a signal Tc as to the transmittivity which is corrected at its middle portion. Then, the following calculation is carried out to obtain a signal Ap proportional to the dot percentage.

$$Ap = (1 - Tc) \times 100 \quad (6)$$

The parts (A) and (B) of FIG. 40 show correction curves obtained by such a process as described above.

A circuit shown in FIG. 41 carries out correction similar to those described with reference to FIG. 39. In this method, a portion $\alpha T = 1$ is not affected. Correction curves obtained in this method are as shown in the parts (A) and (B) of FIG. 42. One of the merits of this method resides in that, as the factor $\alpha$ is adjusted initially in signal processing, the circuit for multiplying the factor $\alpha$ can be replaced by the aperture mechanism and the gain control circuit.

As is apparent from the above description, in the dot percentage measuring device according to the invention, the light receiving section and the dot percentage display section are formed as one unit. Therefore, the dot evaluation can be quickly and positively carried out, the measuring device can be readily operated, and yet its construction is very simple.

Furthermore, according to the invention, the light receiving section is provided in the measuring table in such a manner that the upper edge of the opening in the light receiving section is flush with the upper surface of the measuring table, and the light emitting section adapted to emit the predetermined light to irradiate the object to be measured placed on the measuring table is confronted with the light receiving section. Accordingly, unlike the conventional measuring device described before, the mechanism to vertically move the light receiving section so as to confront the light emitting section can be eliminated. Thus, the construction of the measuring device is much simpler to improve the work efficiency.

Furthermore, according to the invention, the abovedescribed recess and light receiving cylinder are provided at a part of the measuring device. Therefore, the field of vision of the operator is not narrowed in measurement, unlike the case of the conventional measuring device, and the light receiving cylinder can be readily placed on a portion of a test piece to be measured. In general, such measurement is carried out for many portions of the test piece, and a number of test pieces are subjected to the measurement. However, since the light receiving cylinder can be readily operated according to the invention, the operator will not get tired of frequently carried out measurements.

What is claimed is:

1. A dot percentage measuring means comprising:
   a light receiving section provided inside a measuring washing table; and
   a light emitting section adapted to emit a predetermined intensity of light to a radiated object to be measured on said measuring table, said light emitting section being fixedly provided to confront said light receiving section to measure a dot percentage a transmitting density of said object from a quantity of light passed through said object.

* * * * *